United States Patent
Dold et al.

(10) Patent No.: US 10,023,433 B2
(45) Date of Patent: Jul. 17, 2018

(54) MONITORING OF SUPPORT IN ELEVATOR INSTALLATIONS

(71) Applicant: Inventio AG, Hergiswil (CH)

(72) Inventors: Florian Dold, Root (CH); Volker Zapf, Obernau (CH); Wolf Neumann-Henneberg, Rietheim-Weilheim (DE)

(73) Assignee: INVENTIO AG, Hergiswil (CH)

( * ) Notice: Subject to any disclaimer, the term of this patent is extended or adjusted under 35 U.S.C. 154(b) by 220 days.

(21) Appl. No.: 14/437,526

(22) PCT Filed: Oct. 21, 2013

(86) PCT No.: PCT/EP2013/071911
§ 371 (c)(1),
(2) Date: Apr. 22, 2015

(87) PCT Pub. No.: WO2014/064022
PCT Pub. Date: May 1, 2014

(65) Prior Publication Data
US 2015/0291394 A1 Oct. 15, 2015

(30) Foreign Application Priority Data
Oct. 22, 2012 (EP) .................................... 12189370

(51) Int. Cl.
*G01N 27/06* (2006.01)
*B66B 7/12* (2006.01)
(Continued)

(52) U.S. Cl.
CPC ............ *B66B 7/1223* (2013.01); *B66B 7/062* (2013.01); *B66B 7/064* (2013.01); *G01N 27/041* (2013.01); *H01R 24/60* (2013.01)

(58) Field of Classification Search
CPC ....... B66B 7/1223; B66B 7/062; B66B 7/064; G01N 27/041; H01R 24/60
(Continued)

(56) References Cited

U.S. PATENT DOCUMENTS 2,740,735 A * 4/1956 Swain ...................... H01H 1/02
148/532
4,472,018 A * 9/1984 Urani ................... H01H 85/205
439/814

(Continued)

FOREIGN PATENT DOCUMENTS

CA 2778870 A1 7/2011
DE 3934654 A1 5/1991
(Continued)

*Primary Examiner* — Melissa Koval
*Assistant Examiner* — Courtney McDonnough
(74) *Attorney, Agent, or Firm* — William J. Clemens; Shumaker, Loop & Kendrick, LLP (57) ABSTRACT

A support for an elevator car in an elevator installation includes a plurality of tensile carriers, arranged parallel to one another, and a casing. The tensile carriers are enclosed by the casing, wherein the tensile carriers extend along a longitudinal axis of the support. The tensile carriers are freed at least partly from the casing on a section of the longitudinal axis of the support. Contact elements for electrical contacting of the exposed tensile carriers are fastened to the tensile carriers at this section.

18 Claims, 4 Drawing Sheets

(51) Int. Cl.
 *B66B 7/06* (2006.01)
 *G01N 27/04* (2006.01)
 *H01R 24/60* (2011.01)

(58) Field of Classification Search
 USPC .......................... 324/693; 187/413; 439/675
 See application file for complete search history.

(56) References Cited

U.S. PATENT DOCUMENTS

2004/0007901 A1   1/2004  Weik et al.
2011/0220438 A1*  9/2011  Annen .................... B66B 7/062
                                              187/251

FOREIGN PATENT DOCUMENTS

| EP | 2451735 A1 | 5/2012 |
| EP | 2791040 A1 | 10/2014 |
| WO | 2005094249 A2 | 10/2005 |
| WO | 2010057797 A1 | 5/2010 |
| WO | 2011003790 A1 | 1/2011 |
| WO | 2011003791 A1 | 1/2011 |
| WO | 2011098847 A1 | 8/2011 |
| WO | 2013087418 A1 | 6/2013 |

* cited by examiner

MONITORING OF SUPPORT IN ELEVATOR INSTALLATIONS

FIELD

The subject of the invention is monitoring of support means in elevator installations, particularly a support means suitable for monitoring, as well as an elevator installation with such a support means and a method for monitoring a support means.

BACKGROUND

In many conveying devices such as, for example, elevator installations, cranes or hoists use is made of belt-shaped support means. These support means generally comprise a plurality of tensile carriers which consist of steel wires and which accept the tensile forces to be absorbed by the support means. The tensile carriers are generally surrounded by a casing of synthetic material. The casing protects the tensile carriers from, for example, mechanical wear, since the support means are frequently guided around deflection points. In addition, the casing improves the traction of the support means on deflecting or drive rollers and fixes the arrangement of the tensile carriers relative to one another.

Such support means are a safety-relevant component within a conveying device. Failure or breakage thereof can lead to dropping down of the items being conveyed. This can lead to substantial harm to objects or persons. For this reason, use is made of check units in conveying devices, which check, in particular, the mechanical state of the tensile carriers. Damage of the tensile carriers accepting the forces shall thereby be able to be recognized in good time so that the support means in the case of damage can be exchanged in order to prevent failure of the conveying device.

The electrically conductive, metallic tensile carriers are surrounded by the electrically insulating casing of synthetic material. In order to carry out a check of the state of the tensile carriers contacting of a contact element with the tensile carriers is necessary in some methods. In one known method an electrical current, which serves as a test current for the purpose of ascertaining the state of the tensile carriers, is conducted through the tensile carriers with the help of the contact element.

DE 3 934 654 A1 shows a support means of the category described above. The ends of the tensile carriers are in that case conductively connected in pairs with a bridge member so that the tensile carriers of the support means are electrically connected in series. The tensile carriers of the support means are connected with a voltage source by way of an ammeter so that the state of the tensile carriers can be assessed by means of the test current which is conducted through all tensile carriers by virtue of the electrical connection in series.

WO 2005/094249 A2 shows a system for contacting a support means in which the contact elements puncture the casing of the support means perpendicularly to a longitudinal axis of the tensile carriers and then penetrate into the tensile carriers. It can be disadvantageous in that case that the contact elements due to the required puncturing process through the casing miss the tensile carriers. In addition, a transfer resistance between the tensile carriers and the contact elements penetrated therein can change over time which has a disadvantageous effect on the meaningfulness of a monitoring procedure.

WO 2010/057797 A1 and WO 2011/003791 A1 show systems for contacting a support means in which contact elements are mounted on exposed tensile carriers of the support means, for example by resilient contacts or by contact spikes penetrating into the tensile carriers. It is disadvantageous with such contacting systems that the connection between contact elements and tensile carriers is non-constant and that a high transfer resistance between the contact element and the tensile carriers is present.

SUMMARY

An object of the present invention consists in making available a support means which can be monitored in an elevator installation, wherein the tensile carriers of the support means are to be reliably electrically contacted and wherein a low and constant transfer resistance between the tensile carriers and a monitoring device shall be present. A further object of the present invention is to provide a method of monitoring a state of tensile carriers in a support means in which the tensile carriers can be reliably electrically contacted and in which a low and constant transfer resistance between the tensile carriers and a monitoring unit is present. In addition, the method shall allow simple connection of the support means with the monitoring device.

Proposed for fulfillment of this object is a support means for elevator installations, which comprises a plurality of tensile carriers arranged parallel to one another and a casing. In that case, the tensile carriers are enclosed by the casing and the tensile carriers extend along a longitudinal axis of the support means. The tensile carriers are at least partly freed from the casing on a section of the longitudinal axis of the support means. Contact elements for electrical contacting of the tensile carriers are permanently fastened to the tensile carriers on this section.

Such a support means has the advantage that the tensile carriers already have contact elements for electrical contacting of the tensile carriers, so that at the time of installation of the support means in an elevator installation the contact elements merely have to be connected with a monitoring device. Thus, it is no longer necessary for the tensile carriers to be electrically contacted, as is the case in the prior art, at the time of installing the support means in the elevator installation. This significantly simplifies mounting of a monitoring system for support means in elevator installations. In addition, it can be ensured by the contact elements fastened to the tensile carriers that a stable electrical connection with the tensile carriers can be produced and that a low and constant transfer resistance from the tensile carriers to the monitoring device can be ensured. A low and constant transfer resistance allows reliable monitoring of the tensile carriers over the entire period of use thereof in an elevator installation.

In an advantageous embodiment the tensile carriers are completely free from the casing on the section of the longitudinal axis of the support means. This has the advantage that the contact elements can be better fastened to the tensile carriers.

In an advantageous embodiment the section amounts to 5 to 100 millimeters, preferably 5 to 50 millimeters and particularly preferably 5 to 25 millimeters. Such a dimensioning of the section allows an offset arrangement of the contact elements and yet is so dimensioned that the tensile carriers of the support means are not unnecessarily exposed over a longer section. If the section is selected to be too large there is additionally the risk that the tensile carriers are deformed on the section, which can lead to undesired instances of contact of adjacent tensile carriers with one another.

In an advantageous embodiment the section is arranged near an end of the support means so that support means regions with uncased tensile carriers adjoin the section on either side thereof. Such an arrangement of the section has the advantage that the tensile carriers on either side of the section are held in the intended position thereof by the casing. The tensile carriers at the section are thereby prevented from excessive deformation and creation of electrical bridges between the tensile carriers is prevented.

In an alternative embodiment the section is arranged directly at an end of the support means so that a support means region with uncased tensile carriers adjoins the section only on one side thereof. Such an arrangement of the section has the advantage that casing removal at the section can be undertaken more simply. For example, the casing can be interrupted at an intended location and then pulled off the tensile carriers.

The contact elements are permanently connected with the tensile carriers. This has the advantage that the contact elements cannot be lost during storage, transport and installation of the support means. By "permanent connection" there is to be understood in this context a connection which cannot be released without a greater amount of effort. Contact elements penetrating into the tensile carriers accordingly do not form a permanent connection, because they can be extracted from the tensile carriers without a greater amount of effort. Contact elements welded to the tensile carriers accordingly form a permanent connection, because welded parts due to the material couple cannot be separated from one another without a greater expenditure of effort.

In an advantageous embodiment the contact elements at least partly engage around the tensile carriers. This has the advantage that through such an encircling engagement a larger contact area and thereby a more secure electrical connection between contact element and tensile carriers are produced and that in addition a lower transfer resistance between tensile carriers and contact element can be achieved.

In an advantageous form of embodiment the contact elements are soldered, welded or glued to the tensile carriers or are permanently deformed by a mechanical action and thereby fastened to the tensile carriers. This has in turn the advantage that the contact elements remain securely connected with the tensile carriers, whereby a stable electrical connection with a low and constant transfer resistance can be ensured.

In an advantageous embodiment the contact elements project away substantially perpendicularly to the longitudinal axis of the support means. In an advantageous development the contact elements additionally project away substantially perpendicularly to a traction side of the support means. This has the advantage that contact elements thus projecting away from the tensile carriers are readily accessible and can, for example, be connected with a plug mounted on the support means.

In an alternative embodiment in which the section is directly arranged at an end of the support means the contact elements project away substantially in the direction of the tensile carriers. Such an arrangement of the contact elements has the advantage that the contact elements can be tapped in an extension of the support means. Depending on the respective space conditions in the lift elevator installation this can represent an advantage by comparison with a radial form of contacting.

In an advantageous form of embodiment the section lies in a region of the support means which in a use state in an elevator installation is not loaded by an elevator car or a counterweight. It is thereby ensured that supporting regions of the support means are completely encased by the casing and thereby less susceptible to damage.

In an advantageous form of embodiment a first section is arranged in the vicinity of a first end of the support means and a second section is arranged in the vicinity of a second end of the support means. The provision of a respective section with contact elements at each of the two ends of the support means has the advantage that the tensile carriers can be monitored over the entire length of the support means.

In an advantageous embodiment a contact element is arranged at each tensile carrier of the support means. This has the advantage that each tensile carrier of the support means can be monitored, which increases safety of the elevator installation.

In an advantageous embodiment adjacent contact elements are offset relative to one another with respect to the longitudinal axis of the support means. In that case, the contact elements can, for example, be arranged in two rows so that the contact elements are respectively arranged in alternation in a first row and a second row from one side of the support means to the other side of the support means. Such an offset arrangement of the contact elements has the advantage that an electrical contact between two adjacent tensile carriers can be avoided. This is of advantage particularly in the case of support means with tensile carriers lying closely adjacent to one another. In addition, more space for tapping the contact elements arises through an offset arrangement of the contact elements.

In an advantageous embodiment a cover element is arranged over the tensile carriers on the section so that substantially only locations of the tensile carriers at which the contact elements are arranged are freed of the cover element. Such a cover element can be constructed from, for example, a polyamide, preferably from a fiber-reinforced polyamide. In an alternative form of embodiment the cover element is formed from a thermoplastic polyurethane, preferably from a fiber-reinforced thermoplastic polyurethane. Such a cover element has the advantage that the tensile carriers even at the uncased section are protected from environmental influences when the support means is used in an elevator installation. Such a cover element is additionally a protection for the contact elements during transport of the support means and during installation of the support means in the elevator installation. Thus, the contact elements are, for example, protected from undesired kinking or squeezing during looping-in of the support means through a support means end connection.

The support means described here is, in a preferred embodiment, used in an elevator installation with a drive and a car. In that case, the section with the contact elements is so arranged that it comes to lie in a region of the support means which is not loaded by car weight. The support means described here is in principle usable in different kinds of elevator installations. Thus, for example, elevators with or without a counterweight are conceivable, as well as different suspension systems of the car or of the counterweight. The support means described here can thus be used in elevator installations in which the car has 2:1 suspension as well as in elevator installations in which the car and the counterweight have 1:1 suspension and also in other forms of design of the installations.

In an advantageous embodiment the contact elements are electrically connected with a monitoring unit of an elevator installation. Such a monitoring device can, for example, check an electrical resistance of the individual tensile carriers.

In an advantageous embodiment the contact elements are formed from a galvanized metal plate. In an advantageous development this metal plate is bent so that two limbs are created, which in a use state clasp around the tensile carriers. In an alternative form of embodiment the contact elements are formed from a tinned or stainless-steel metal plate.

In addition, a method for monitoring a state of tensile carriers in a support means is proposed for fulfillment of the object expressed in the introduction, wherein the support means comprises a plurality of tensile carriers arranged parallel to one another. In addition, the support means comprises a casing, wherein the tensile carriers are enclosed by the casing. The method comprises the following steps: at least partly freeing the tensile carriers at a section of the support means; permanent fastening of contact elements to the tensile carriers at the freed section of the support means for electrical contacting of the tensile carriers; installing the support means in an elevator installation; connecting the contact elements with a monitoring unit; and determining an electrical characteristic value of the tensile carriers for monitoring the state of the tensile carriers.

Such a method has the advantage that the fastening of the contact elements to the tensile carriers can be carried out before installation of the support means in the elevator installation. The support means can thus be pre-fitted with the contact elements, which substantially simplifies mounting of a monitoring system in the elevator installation. In addition, such contact elements fastened at the factory can produce a more secure electrical connection with the tensile carriers as well as ensure a lower and more constant transfer resistance between contact elements and tensile carriers.

In an advantageous embodiment, for the freeing of the tensile carriers the casing is brushed at the section and/or cut by water jet. In an advantageous development the casing is initially brushed on the section, then cut by water jet and then brushed again. Such a freeing process guarantees tensile carriers which are cleanly freed from the casing and at which a secure electrical connection characterized by a small transfer resistance can be formed. In addition, the section can be freed by such a freeing method through brushing or water-jet cutting with a tolerance required here.

In an alternative embodiment, for freeing of the tensile carriers the casing is melted at the section by thermal action.

In a further alternative embodiment, for freeing of the tensile carriers the casing is removed at the section by a laser.

In a further alternative embodiment the casing is cut at an intended location and then pulled off the tensile carriers. In that case the casing can be pulled completely off the tensile carriers, whereby the freed section is the present directly at the end of the support means, or the casing can be pulled incompletely off the tensile carriers, whereby the partly pulled-off casing protrudes beyond the end so that the freed section is not directly present at the end of the support means.

In an advantageous embodiment the contact elements are welded, soldered or glued to the tensile carriers or permanently deformed by a mechanical action and thereby fastened to the tensile carriers. Contact elements fastened in such a way represent a secure electrical connection with a low and constant transfer resistance between the tensile carriers and the contact elements.

In an advantageous embodiment a cover element is arranged over the tensile carriers before or after fastening of the contact elements to the tensile carriers, so that substantially only locations of the tensile carriers at which the contact elements are arranged are freed of the cover element. Such a cover element protects the contact elements from environmental influences during operation in an elevator installation and during transport as well as installing of the support means in an elevator installation.

In an advantageous embodiment, through the installing of the support means in the elevator installation the section with the contact elements lies at a region which is not loaded by a car weight or a counterweight. Unnecessary weakening of the support means in a load-bearing region is thereby prevented. In addition, vibrations of the support means, which would have a disadvantageous effect on the electrical connection can thereby be largely excluded.

In addition, a plug with a base and a cover is proposed for electrical tapping of a support means, which is described here, with contact elements.

In an advantageous embodiment the contact elements are electrically tapped by connecting elements in the plug. On fastening of the plug to the support means or to the contact elements initially the support means with the contact elements is laid in the base. In that case the support means is mounted in the base to be movable not only in the direction of the tensile carriers, but also transversely to the direction of the tensile carriers within close limits. If now the cover with the connecting elements is fastened to the base the support means thus appropriately aligns itself in the base, during which the connecting elements come into contact with the contact elements in intended mode and manner. After the support means is appropriately aligned in the base and the connecting elements are in contact with the contact elements in intended mode and manner the cover and base are fastened to one another. Through fastening of the cover to the base the connecting elements are retained in the intended position thereof with respect to the contact elements. By way of such a plug the contact elements can be electrically tapped reliably and in a protected frame.

In an advantageous embodiment the connecting elements are so constructed that the connecting elements contact the contact elements at four or more points when the connecting elements are in contact with the contact elements in intended mode and manner. This has the advantage that a low transfer resistance can be achieved by a higher number of contact points between the contact element and the connecting elements.

DESCRIPTION OF THE DRAWINGS

Details and advantages of the invention are described in the following by way of embodiments and with reference to schematic drawings, in which.

DETAILED DESCRIPTION

Figure 1:
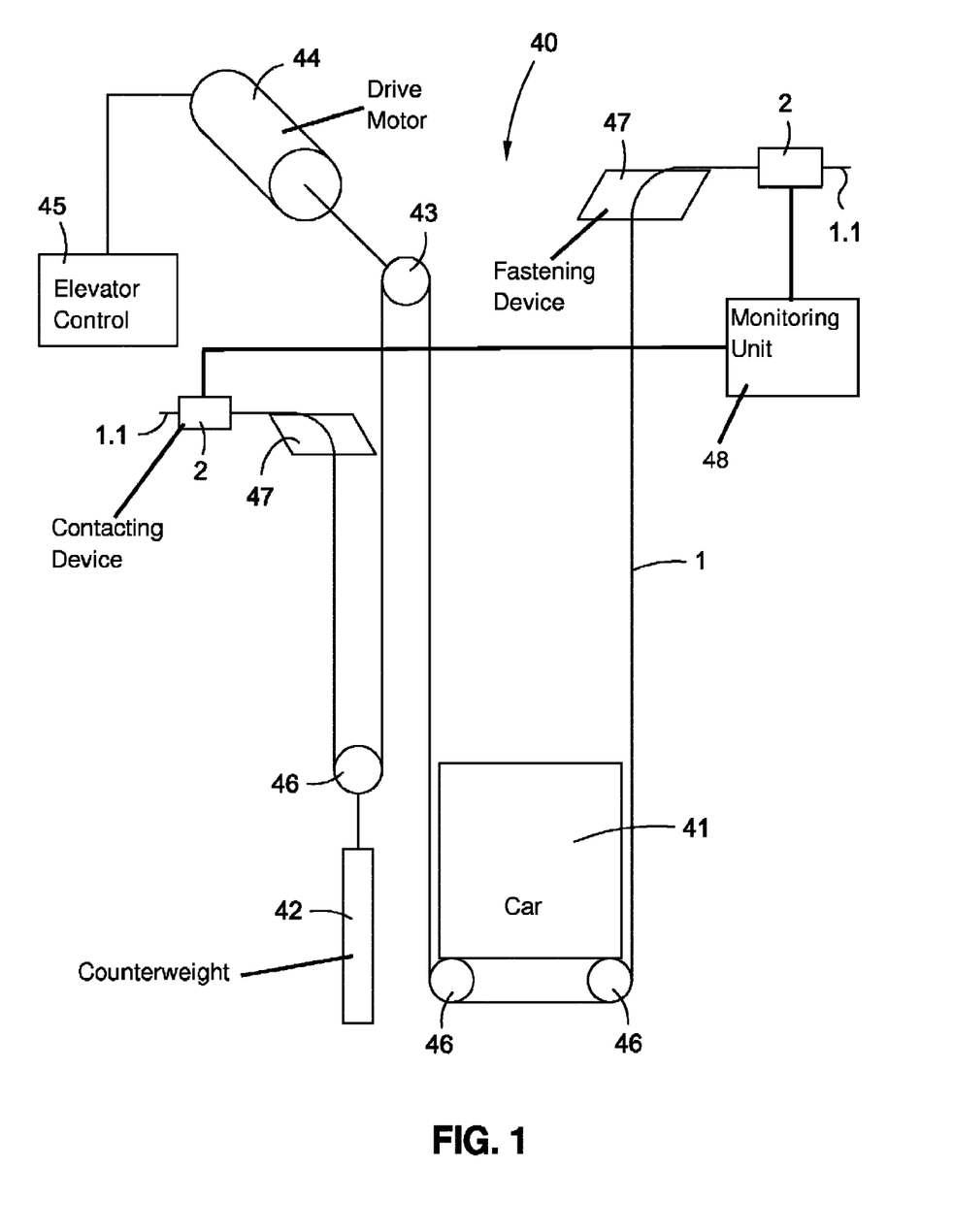
FIG. 1 shows an exemplifying form of embodiment of an elevator installation.

The elevator installation 40 illustrated schematically and by way of example in FIG. 1 includes an elevator car 41, a counterweight 42 and a support means 1 as well as a drive pulley 43 with associated drive motor 44. The drive pulley 43 drives the support means 1 and thus moves the elevator car 41 and the counterweight 42 in opposite sense. The drive motor 44 is controlled by an elevator control 45. The car 41 is designed to receive persons and/or goods and to transport them between floors of a building. The car 41 and counterweight 42 are guided along guides (not illustrated). In the example the car 41 and the counterweight 42 are each suspended at support rollers 46. The support means 1 is in that case fixed at a first support means fastening device 47 and then guided initially around the support roller 46 of the counterweight 42. The support means 1 is then laid over the drive pulley 43, guided around the support rollers 46 of the car 41 and finally connected by a second support means fastening device 47 to a fixing point. This means that the support means 1 runs over the drive 43, 44 at a speed which is higher, in correspondence with a suspension factor, than the car 41 and counterweight 42 move. In the example the suspension factor is 2:1.

A free end 1.1 of the support means 1 is provided with a contacting device 2 for temporary or permanent contacting of the support means 1. In the illustrated example a contacting device 2 of that kind is arranged at both ends of the support means 1. In an alternative form of embodiment (not illustrated) only one contacting device 2 is arranged at one of the support means ends 1.1. The support means ends 1.1 are no longer loaded by the tension force in the support means 1, since this tension force is already conducted in advance into the building by way of the support means fastening devices 47.

The contacting devices 2 are thus arranged in a region, which is not rolled over, of the support means 1. The contacting devices 2 are electrically connected with a monitoring unit 48 for checking the electrical resistance of individual tensile carriers in the support means 1.

The illustrated elevator installation 40 in FIG. 1 is by way of example. Other suspension factors and arrangements such as, for example, elevator installations without a counterweight are possible. The contacting device 2 for contacting the support means 1 is then arranged in correspondence with the positioning of the support means fastening devices 47.

Figure 2:
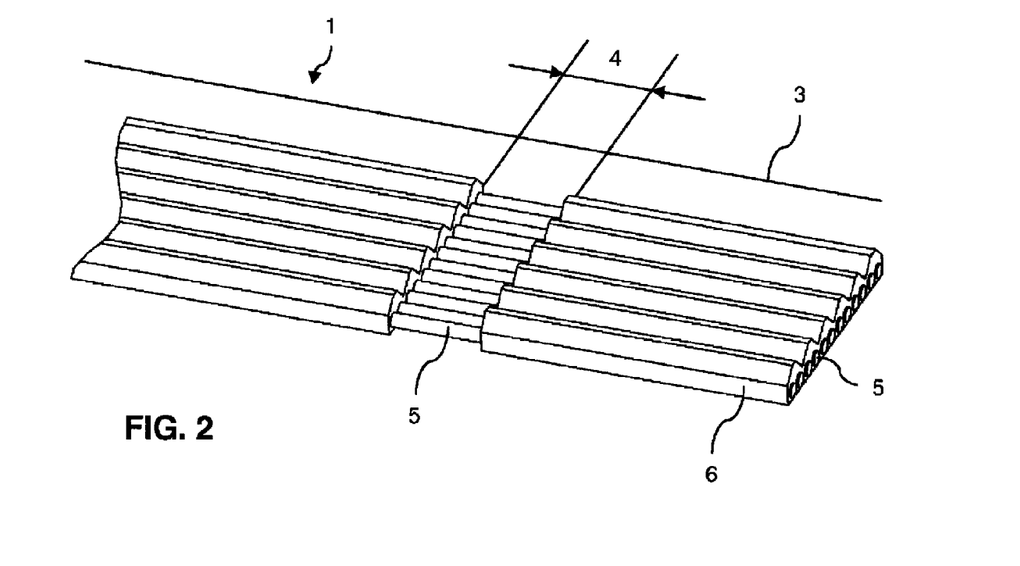
FIG. 2 shows an exemplifying form of embodiment of a support means with a freed section.

An exemplifying form of embodiment of a support means 1, formed as a belt-shaped support, with tensile carriers 5 and an enclosing casing 6 is illustrated in FIG. 2. In that case, the tensile carriers 5 are arranged along a longitudinal axis 3 of the support means 1. The tensile carriers 5 are freed from the casing 6 at a section 4 of the longitudinal axis 3 of the support means. The support means illustrated in this example has longitudinal ribs on a traction side. In an alternative embodiment, which is not illustrated, the support means does not have any longitudinal ribs.

The freeing of the tensile carriers 5 at the section 4 can be carried out, for example, by brushing and/or cutting by water jet. In an exemplifying form of embodiment initially one side of the casing 6 is brushed away up to the tensile carriers 5. A second side is then similarly brushed away up to the tensile carriers 5. The remaining casing 6 is subsequently cut away at the section 4 by water-jet cutting. The water-jet cutting is preferably carried out in axial direction with respect to the longitudinal axis 3 of the support means 1 and parallelly to the tensile carriers 5. In that case, a diameter of the water jet lies between, for example, 0.3 and 0.7 millimeters. In order to completely free the tensile carriers from the casing 6 a brushing process can again be provided after the cutting with water jet. Such a downstream brushing process ensures that the casing 6 is completely removed on the section 4. A complete removal of the casing 6 on the section 4 is important for reliable electrical contacting of the tensile carriers 5 by the contact elements 8 (shown in FIG. 3).

Figure 3:
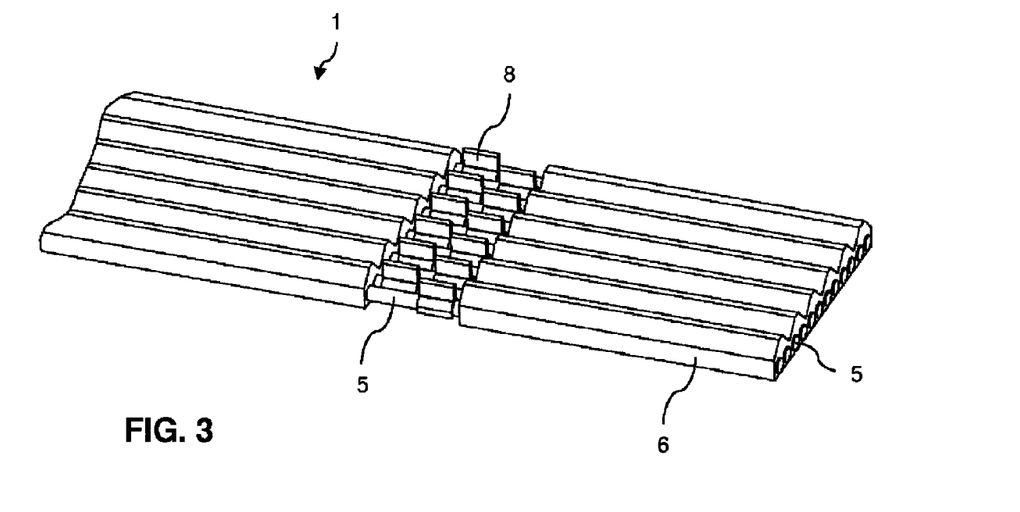
FIG. 3 shows an exemplifying form of embodiment of a support means with a freed section, wherein contact elements are arranged at tensile carriers.

The same support means 1 as in FIG. 2 is illustrated in FIG. 3. Here, contact elements 8 are fastened to the tensile carriers 5 on the freed section 4. In this embodiment the contact elements 8 are arranged to be offset relative to one another with respect to the longitudinal axis 3 of the support means 1. Contact of adjacent contact elements 8 is thereby prevented and formation of an electrical bridge between adjacent tensile carriers 5 is thereby prevented.

Figure 4:
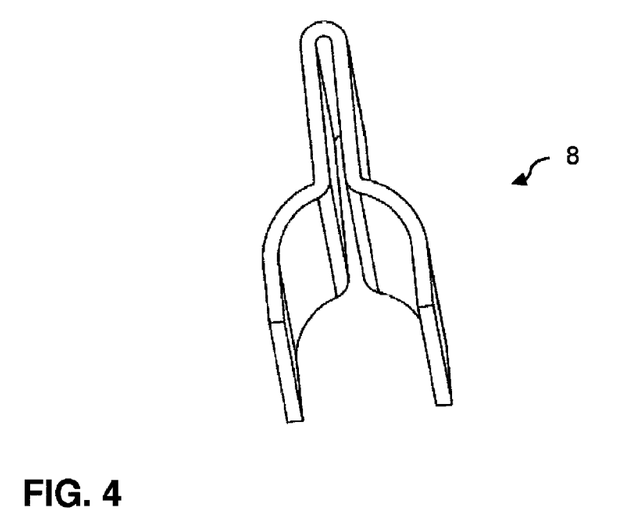
FIG. 4 shows an exemplifying form of embodiment of a contact element.

An exemplifying contact element 8 is illustrated in FIG. 4. The contact element 8 can be formed from a galvanized steel plate, which is appropriately bent. The bent limbs of the contact element 8 serve for clasping around the tensile carriers 5 for producing a secure electrical contact between the contact elements 8 and the tensile carriers 5. The contact elements 8 can, for example, be spot-welded to a tensile carrier 5 at two to four points by a laser.

Figure 5:
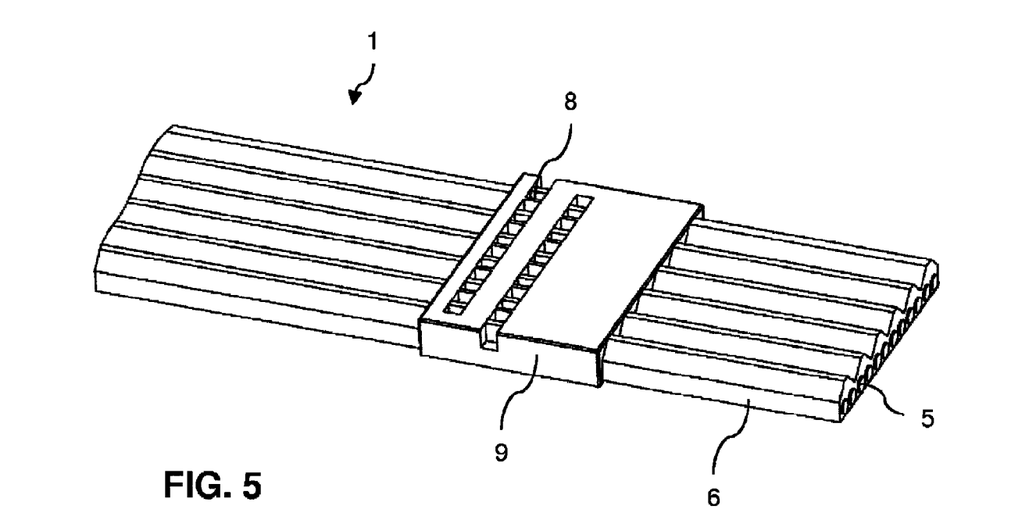
FIG. 5 shows an exemplifying form of embodiment of a support means with a cover.

The same support means 1 as in FIG. 3 is illustrated in FIG. 5, but here a cover element 9 is arranged over the freed section 4. This cover element 9 can be constructed from, for example, polyamide, preferably fiber-reinforced polyamide. The cover element 9 leaves the contact elements 8 free to such an extent that these can be contacted in simple mode and manner by a plug. At the same time, the cover element 9 protects the contact elements 8 from mechanical influences and also protects the freed tensile carriers 5 from environmental influences.

Figure 6:
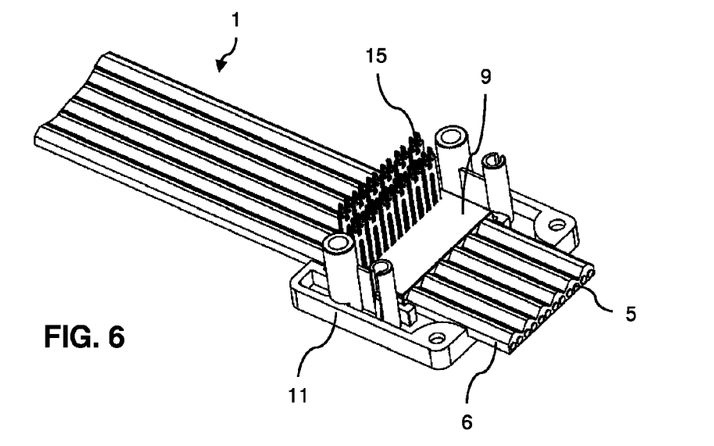
FIG. 6 shows an exemplifying form of embodiment of a support means with contact elements and with a base of a plug.
Figure 7:
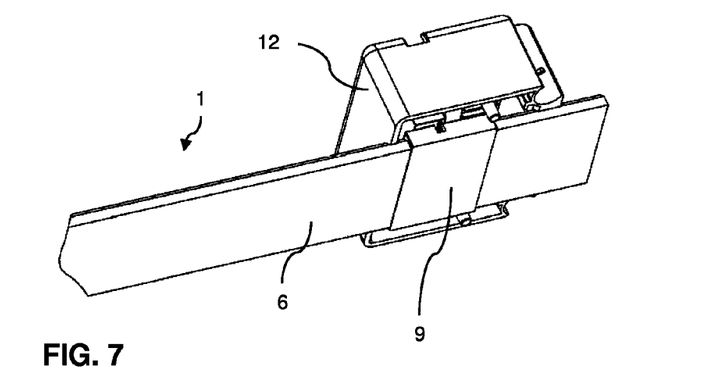
FIG. 7 shows an exemplifying form of embodiment of a support means with contact elements and with a cover of a plug.
Figure 8:
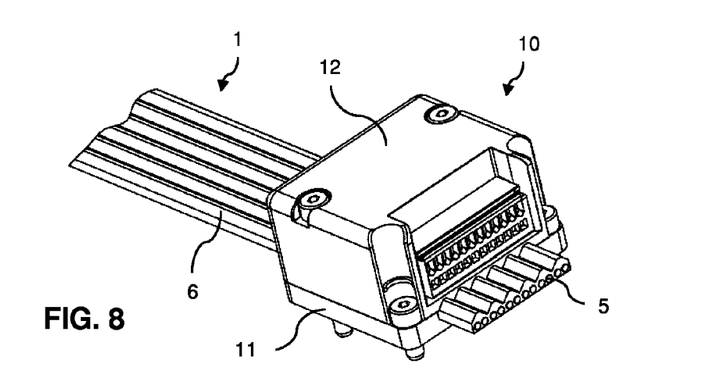
FIG. 8 shows an exemplifying form of embodiment of a support means with contact elements and with a plug arranged thereon.

An exemplifying support means 1 with contact elements 8 (not visible) and with a plug 10 is illustrated in FIGS. 6, 7 and 8. In that case, FIG. 8 shows the complete plug 10, FIG. 6 shows merely a base 11 of the plug 10 and FIG. 7 shows merely a cover 12 of the plug 10. In order to be able to reliably electrically tap the contact elements 8, connecting elements 15 are provided. For connection of the plug 10 with the contact elements 8 initially, for example, the support means 1 can be placed in the base 11. In that case the support means 1 is mounted in the base 11 to be movable within tight limits not only in the direction of the tensile carriers 5, but also transversely to the direction of the tensile carriers 5. If now the cover 12 with the connecting elements 15 is fastened on the base 11, then the support means 1 appropriately aligns itself in the base 11, during which the connecting elements 15 come into contact with the contact elements 8 in intended mode and manner (in FIG. 6 the connecting elements 15 are, for the sake of better clarity, illustrated without the cover 12). After the support means 1 is appropriately aligned in the base 11 and the connecting elements 15 come into contact with the contact elements 8 in intended mode and manner the cover 12 is screw-connected with the base 11. The plug 10 finally mounted on the support means 1 protects the freed support means section 4 and electrically taps the contact elements 8. The plug 10 can then be electrically connected with a monitoring unit (48 in FIG. 1).

The plug 10 illustrated in FIGS. 6 to 8 forms, together with the contact elements 8, an exemplifying contacting device 2 as is schematically illustrated in FIG. 1.

In accordance with the provisions of the patent statutes, the present invention has been described in what is considered to represent its preferred embodiment. However, it should be noted that the invention can be practiced otherwise than as specifically illustrated and described without departing from its spirit or scope.

The invention claimed is:

1. A support for an elevator installation, comprising: a plurality of electrically conductive tensile carriers arranged parallel to one another; a casing enclosing the tensile carriers wherein the tensile carriers extend along a longitudinal axis of the support, and wherein the tensile carriers are freed at least partly from the casting on a section along the longitudinal axis of the support; and a plurality of contact elements for electrical contacting of the tensile carriers, each of the contact elements being permanently fastened to the tensile carriers at the section to form a permanent connection between the contact element and the tensile carrier; wherein the contact elements are fastened to the tensile carriers by at least one of soldered, welded, glued and permanently deformed by a mechanical action.

2. The support according to claim 1 wherein the contact elements project away from the tensile carriers substantially perpendicularly to the longitudinal axis of the support.

3. The support according to claim 1 wherein the contact elements project away from the tensile carriers substantially perpendicularly to a traction side of the support.

4. The support according to claim 1 wherein at least one of the contact elements is arranged at each of the tensile carriers.

5. The support according to claim 1 wherein adjacent ones of the contact elements are arranged offset relative to one another with respect to the longitudinal axis of the support.

6. The support according to claim 1 including a cover element arranged over the tensile carriers at the section and configured so that substantially only locations of the tensile carriers at which the contact elements are fastened are freed from the cover element.

7. The support according to claim 1 wherein the section measures in a range of 5 to 100 millimeters in a direction of the longitudinal axis of the support.

8. An elevator installation with a support according to claim 1 suspending an elevator car.

9. A plug for electrical tapping of a support according to claim 1, the plug including a base and a cover, wherein when the support with the contact elements is arranged in the base the support is movable in a direction of the longitudinal axis and transversely to the longitudinal axis, wherein the cover includes connecting elements, wherein when the cover is arranged on the base the support aligns in the base whereby the connecting elements come into contact with the contact elements, and when the cover and base are fastened to one another the connecting elements are held in contact with the contact elements.

10. The support according to claim 1 wherein each of the contact elements forms a material couple with one of the tensile carriers, the material couple requiring a force to separate.

11. The support according to claim 1 wherein each of the contact elements at least partly engages around one of the tensile carriers.

12. The support according to claim 1 wherein each of the contact elements includes two limbs that clasp around one of the tensile carriers.

13. The support according to claim 12 wherein each of the contact elements includes a metal plate that is bent to create the two limbs that clasp around one of the tensile carriers.

14. The support according to claim 13 wherein each of the contact elements is spot welded to one of the tensile carriers.

15. A method of monitoring a state of tensile carriers in a support, wherein the support includes a plurality of the tensile carriers arranged parallel to one another and a casing enclosing the tensile carriers, comprising the steps of: at least partly freeing the tensile carriers on a section of the support; permanently fastening contact elements to the tensile carriers in the freed section of the support means to form permanent connections between the contact elements and the tensile carriers and for electrical contacting of the tensile carriers; installing the support in an elevator installation; connecting the contact elements with a monitoring unit; and determining an electrical characteristic value of the tensile carriers with the monitoring unit for monitoring the state of the tensile carriers; wherein the contact elements are fastened to the tensile carriers by at least one of soldered, welded, glued and permanently deformed by a mechanical action.

16. The method according to claim 15 wherein for the freeing of the tensile carriers the casing at the section is at least one of brushed, cut by water jet, melted, removed by laser and a portion of the casing is at least partly pulled off the tensile carriers.

17. The method according to claim 15 wherein the casing is initially brushed at the section, then cut by water jet and then brushed again.

18. The method according to claim 15 wherein before or after fastening of the contact elements to the tensile carriers, a cover element is arranged over the tensile carriers so that substantially only locations of the tensile carriers at which the contact elements are arranged are freed.

* * * * *